United States Patent
Rasochova

(10) Patent No.: US 11,103,443 B2
(45) Date of Patent: Aug. 31, 2021

(54) COMPOSITIONS AND METHODS FOR PREVENTING, SLOWING, AND REVERSING SKIN AGING

(71) Applicant: Dermala, San Diego, CA (US)

(72) Inventor: Lada Rasochova, Del Mar, CA (US)

( * ) Notice: Subject to any disclaimer, the term of this patent is extended or adjusted under 35 U.S.C. 154(b) by 0 days.

(21) Appl. No.: 16/614,635

(22) PCT Filed: May 22, 2018

(86) PCT No.: PCT/US2018/033984
§ 371 (c)(1),
(2) Date: Nov. 18, 2019

(87) PCT Pub. No.: WO2018/217826
PCT Pub. Date: Nov. 29, 2018

(65) Prior Publication Data
US 2020/0179266 A1 Jun. 11, 2020

Related U.S. Application Data

(60) Provisional application No. 62/509,717, filed on May 22, 2017.

(51) Int. Cl.
| | |
|---|---|
| *A61K 8/9706* | (2017.01) |
| *A61K 8/9794* | (2017.01) |
| *A61K 8/9789* | (2017.01) |
| *A61K 8/34* | (2006.01) |
| *A61K 8/35* | (2006.01) |
| *A61K 8/64* | (2006.01) |
| *A61K 8/73* | (2006.01) |
| *A61K 8/99* | (2017.01) |
| *A61Q 19/08* | (2006.01) |

(52) U.S. Cl.
CPC ............ *A61K 8/9706* (2017.08); *A61K 8/342* (2013.01); *A61K 8/345* (2013.01); *A61K 8/355* (2013.01); *A61K 8/64* (2013.01); *A61K 8/735* (2013.01); *A61K 8/9789* (2017.08); *A61K 8/9794* (2017.08); *A61K 8/99* (2013.01); *A61Q 19/08* (2013.01)

(58) Field of Classification Search
None
See application file for complete search history.

(56) References Cited

U.S. PATENT DOCUMENTS

2015/0374607 A1 12/2015 Lanzalaco et al.
2016/0000701 A1* 1/2016 Qvit-Raz ................. A61K 8/27
424/60

FOREIGN PATENT DOCUMENTS

WO WO 2016/172196 A1 10/2016
WO WO 2017/063066 A1 4/2017

* cited by examiner

*Primary Examiner* — Brian Gangle
(74) *Attorney, Agent, or Firm* — Torrey Pines Law Group, PC

(57) ABSTRACT

Disclosed are methods of treating aging effects on a subject skin, comprising contacting the skin with a skin microbiome complex, including topical compositions containing YM Microbiome Complex and Advanced Probiotic Complex, methods of treatment using the compositions and methods of preparing the compositions for preventing, slowing, and reversing skin aging. Also disclosed are related formulations and methods of skin microbiome transplantation.

10 Claims, 2 Drawing Sheets

COMPOSITIONS AND METHODS FOR PREVENTING, SLOWING, AND REVERSING SKIN AGING

CROSS-REFERENCE TO RELATED APPLICATIONS

The present application is a continuation of International App. No. PCT/US18/33984, entitled "COMPOSITIONS AND METHODS FOR PREVENTING, SLOWING, AND REVERSING SKIN AGING" filed on May 22, 2018 which published in English as WO 2018/217826 on Nov. 29, 2018, which claims priority to U.S. Provisional App. No. 62/509, 717, entitled "COMPOSITIONS AND METHODS FOR PREVENTING, SLOWING, AND REVERSING SKIN AGING" filed on May 22, 2017, which are each expressly incorporated by reference in their entirety.

STATEMENT REGARDING FEDERALLY SPONSORED RESEARCH OR DEVELOPMENT

Not Applicable.

FIELD

Disclosed are topical compositions containing YM Microbiome Complex and Advanced Probiotic Complex, methods of treatment using the compositions and methods of preparing the compositions for preventing, slowing, and reversing skin aging.

INTRODUCTION

Aging process results in various changes on the skin. These changes include wrinkles, lines, frown lines, loss of hydration, loss of elasticity, skin sagging, blemishes and pigmentation changes.

The purpose of anti-aging skincare products is to prevent or slow down signs of aging as far as possible. Anti-aging topical skincare products typically contain moisturizing ingredients and anti-aging ingredients such as retinoids (vitamin A derivatives that unclog pores, boost collagen to reduce fine lines, and speed cell turnover to even out discoloration and smooth the skin, for example retinol retinA, retinyl palmitate), Epidermal Growth Factor (has been shown to reduce fine lines, wrinkles and sagging, has healing (wounds and burns) and anti-inflammatory properties when applied to skin), alpha hydroxy acid (AHAs) and beta hydroxy acids (glycolic, lactic, citric and mandelic acids can help peel away the top layers of the skin to erase fine lines), exfoliants, peptides (argireline, copper peptides), coenzyme Q10, anti-oxidants (protect cells from the damage caused by unstable molecules known as free radicals), niacinamide, hyaluronic acid, polylactic acid, *Boswellia serrata*, sunscreens, vitamin C and botulinum toxin. The effects of these ingredients typically depend on their concentration and mode of application. Generally, over the counter anti-aging products lack in effectiveness and the results are disappointing.

Therefore, what is needed is a new treatment for aging, and the effects of aging, on a subject's skin.

SUMMARY

The present teachings include methods for treating aging effects on a subject skin, the method comprising contacting the skin with a skin microbiome metabolite.

These and other features, aspects and advantages of the present teachings will become better understood with reference to the following description, examples and appended claims.

FIGURES

Figure 1:
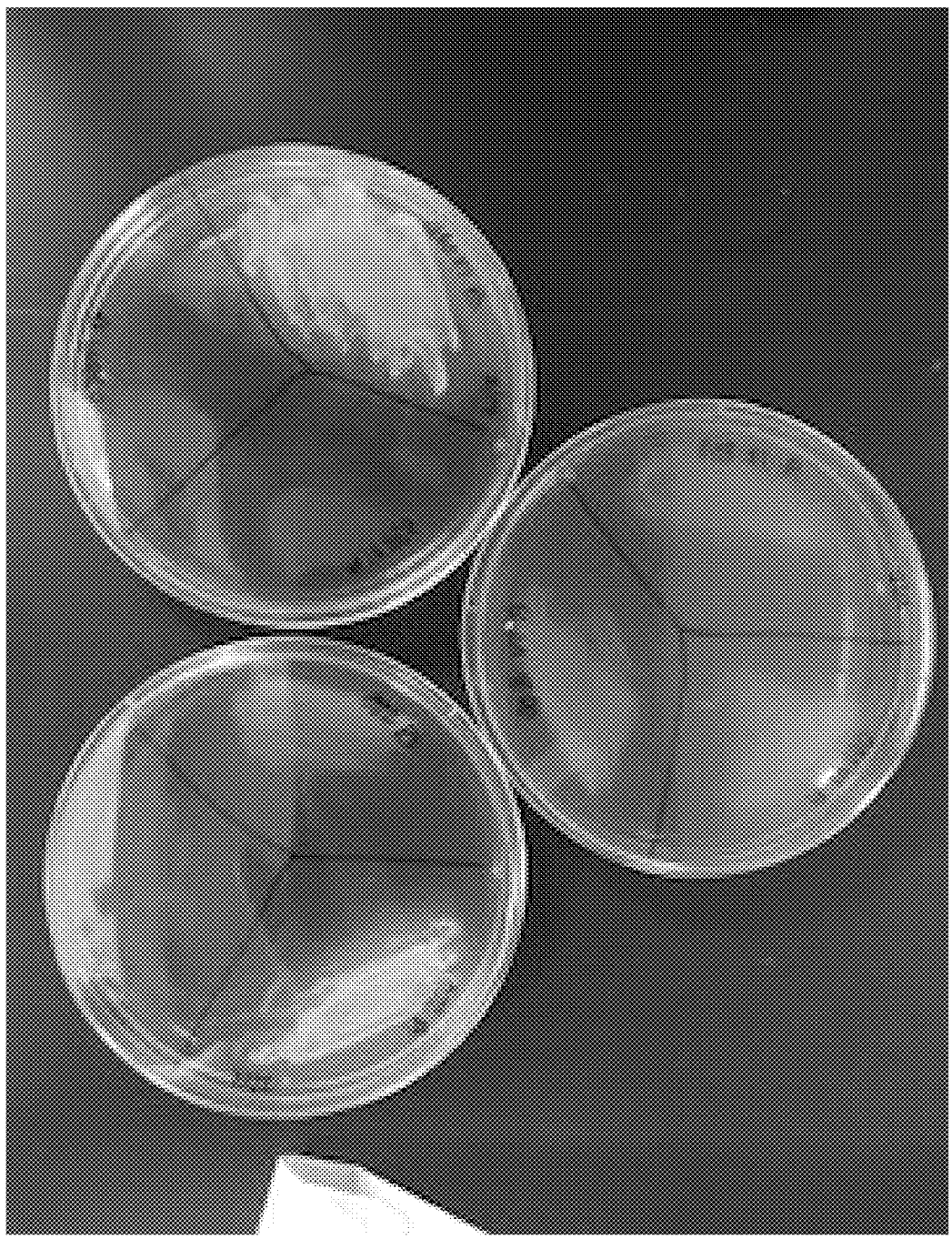

FIG. 1. Isolates from the surface skin of an individual with healthy radiant skin were grown on Mannitol Salt agar for the initial identification of *S. epidermidis* species. Isolates that grew well on the agar without producing a color change were likely *S. epidermidis* species.

Figure 2:
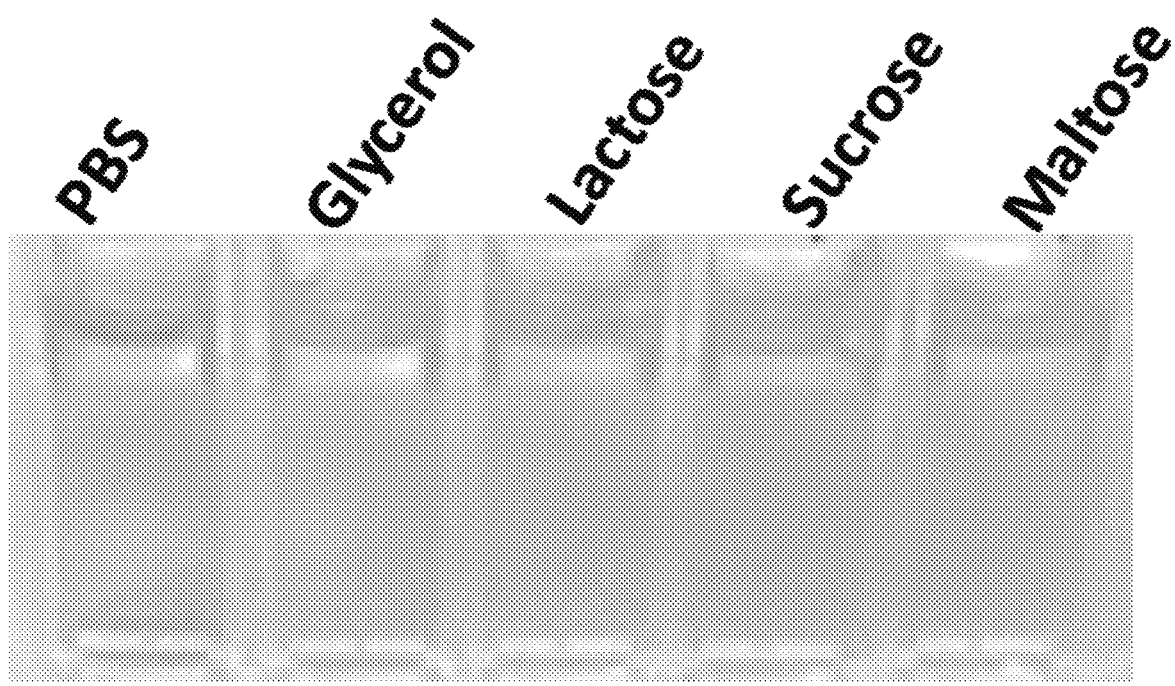

FIG. 2. *S. epidermidis* isolate MK022B cultures grown with 2% PBS, glycerol, β-lactose, sucrose and D-(+)-maltose under anaerobic conditions for 14 days. The change of color from red to yellow in the cultures suggest fermentation has occurred compared to the PBS control.

DETAILED DESCRIPTION

Skin aging can comprise changes in the ceramides content in the skin. Ceramides are the main component of the stratum corneum of the epidermis layer of human skin. Ceramides are a family of waxy lipid molecules. A ceramide is composed of sphingosine and a fatty acid. Together with cholesterol and saturated fatty acids, ceramide creates a water-impermeable, protective organ to prevent excessive water loss due to evaporation as well as a barrier against the entry of microorganisms. As a bioactive lipid, ceramide has been implicated in a variety of physiological functions including apoptosis, cell growth arrest, differentiation, cell senescence, cell migration and adhesion. With aging, there is a decline in ceramide and cholesterol in the stratum corneum of humans.

There are three major pathways known to lead to ceramide generation. The sphingomyelinase pathway uses an enzyme to break down sphingomyelin in the cell membrane and release ceramide. The de novo pathway creates ceramide from less complex molecules. Ceramide generation can also occur through a Salvage pathway which includes breakdown of complex sphingolipids that are ultimately broken down into sphingosine, which is then reused by reacylation to form ceramide. There are several substances known to induce ceramide generation including Anandamide, Ceramidase Inhibitors, Chemotherapeutic agents, Fas ligand, Endotoxin, homocysteine, heat, gamma interferon, ionizing radiation, matrix metalloproteinases, reactive oxygen species, Tetrahydrocannabinol and other Cannabinoids, TNF-alpha, and vitamin D.

The human microbiome also changes with the age. Such changes include changes in the skin microbiome and gut microbiome. The human microbiome is the collection of microbes on and in human bodies. Skin aging is associated with changes in skin microbial communities. Striking differences in the skin microbiome develop with aging. These differences have been observed between age groups of young and older adults using bacterial 16S rRNA gene sequencing. The human microbiome contains beneficial microbes that are important for good health. For example, various kin diseases are associated with various defects (dysbiosis) in the skin microbiome. Acne vulgaris is associated with *P. acnes* proliferation in follicles, atopic dermatitis is associated with *S. aureus* overgrowth in eczema skin patches. Reduction in the pathogenic microbes (killing *P. acnes* with benzoyl peroxide or killing *S. aureus* with bleach baths) and balancing the microbiome back to normal state is associated with reduction in diseases symptoms. In addition, various skin diseases as well as aging are associated with dysbiosis in the gut microbiome that leads to inflammation and increased disease severity. Reducing the dysbiosis improves disease symptoms.

In addition to the microbes themselves, the human microbiome contains various metabolites that are produced by the microbes and secreted. These metabolites can be small molecules, peptides, large molecules, such as proteins, and other molecules. These molecules play a role in maintaining the microbiome balance via a phenomenon known as bacterial interference.

Application of extracts from various bacteria such as *Lactobacillus* or *Streptococcus thermophiles* on the skin has been suggested previously. However, no products have been developed that result in the changes in the skin or gut microbiome that would have anti-aging effects on the skin. Skin microbiome metabolites and prebiotics that support production of anti-aging metabolites by bacteria on the skin have not been formulated into anti-ageing products before, and skin microbiome transplants have not been performed for anti-aging purposes In the present invention, we describe using the human microbiome to slow down the process of aging of the skin. We have identified compositions of skin and gut microbiomes, microbiome complexes and metabolites from the skin microbiomes and methods of their production that reduce appearance of skin fine lines and wrinkles, increases hydration, increase ceramide production, increase collagen production, reduces inflammation, improve wound healing, improve skin barrier function, improve skin elasticity, improve stratum corneum flexibility, and reduce and slow down processes associated with skin aging. These composition of metabolites from the skin microbiome may contain one or more metabolites from the skin microbiome.

The composition of metabolites derived from the skin microbiome may further include one or more prebiotic compounds that support the growth and fermentation of skin bacteria producing the metabolite(s) with anti-aging properties.

The composition of metabolites derived from the skin microbiome may further include one or more skin microbiome bacteria.

The composition of one or more bacteria in the skin microbiomes that are found on young, healthy, radiant and wrinkle-free skin.

We have also developed combination products that include composition of skin microbiome metabolites in combination with other anti-aging compounds. An example of such combination product is a combination with retinoids that show synergistic effects in respect to the level of fine line reduction, hydration, improvement in skin color and skin properties including elasticity, and reduction of inflammation.

We have also developed derivatives of the skin microbiome metabolites, including prodrugs, that slow the process of skin ageing after topical application to the skin.

We have also developed formulations of skin metabolites that deliver the skin microbiome metabolites to allow contact with proliferating keratinocytes that form in the stratum basale as they migrate through the epidermis towards the surface and stratum corneum.

We have developed a method of using transplantation of skin microbiomes isolated from young, radiant, wrinkle-free skin (or their synthetic equivalents) onto an aging skin for the purpose of slowing aging and to achieving healthier complexion.

We have also developed compositions of probiotics that balance the gut microbiome and result in improvement of skin health and appearance including increased hydration, elasticity, and reduced inflammation and UV damage.

We have also developed a method of treatment that slows down the process of skin ageing that consists of application of topical skin products for improving the composition of skin microbiome and taking probiotics to improve the composition of gut microbiome.

EXAMPLES

Example 1: Preparation of YM (Young Microbiome)

The ESwab sample collection kit (BD 220245, Becton Dickinson) was used to collect the entire surface skin microbiome samples from healthy individuals of 18-28 yrs old with healthy radiant, blemish-free complexion. The area of the cheek beside the nostril was used as a sample collection site. One hand was used to stretch the skin area to be swabbed (4 $cm^2$) and the other hand was used to rub the swab back and forth for 30 seconds, applying firm pressure to the skin. The swab was inserted into the tube from the ESwab sample collection kit according to manufacturer's protocol and stored at room temperature until processed (within 48 hours). The preparation was designated YM (Young Microbiome).

Example 2; Preparation of YM Complexes

The YM Complex was produced from bacteria present in the YM skin microbiome by growing the bacteria under various conditions aerobically and anaerobically for 1-14 days at 37° C. One condition tested was incubation in trypic soy broth (TSB) at 37° C. and 215 RPM overnight. The overnight culture was subcultured 1:100 in fresh TSB. Once mid-log phase was reached, the cells were pelleted by centrifugation, washed and resuspended in fresh PBS. In 15 ml culture tubes, 4.9 ml of Rich Broth (20 g/L yeast extract, 6 g/L TSB) was combined with 5 ml of 4% prebiotic (glycerol, sucrose, β-lactose, or D-(+)-maltose) or PBS as a control, and YM microbiome inoculum ($10^5$ CFU/ml) and placed in an anaerobic Gas-Pak (BD). The cultures were incubated at 37° C., 215 RPM for 14 days. Various carbohydrates that were included in the media as prebiotics promoted fermentation processes. These included glycerol, sucrose, β-lactose, and D-(+)-maltose, galactose and other carbohydrates. The prebiotics were purchased from Sigma-Aldrich. Stock solutions of each prebiotic (4% w/v) were prepared in water and filtered through a 0.22 μm filter for sterilization.

After incubation, the bacteria were spun down at 4,000 rpm for 10 min at 4 C and the supernatant (designated as YM Complex) was filter sterilized through a 0.22 μm filter and used for further testing. The YM Microbiome Complex included molecules secreted by the skin microbiome bacteria. Alternatively, the YM Microbiome Complex was fractionated using HLPC prior to testing. Alternatively, the bacterial suspension was sonicated two times prior to spinning to also include molecules that were not secreted into the media during the bacterial cultivation. Alternatively, individual bacterial strains from the YM Microbiome such as *S. epidermidis* were used for preparation of the complex. Alternatively, individual metabolites produced by the skin microbiome bacteria were used for preparation of the complex.

Example 3: Isolation of S. epidermidis Isolates from YM Microbiome

The ESwab sample collection kit (BD 220245, Becton Dickinson) was used to collect the entire surface skin microbiome samples from healthy individuals of 18-28 yrs old with healthy radiant skin. The area of the cheek beside the nostril was used as a sample collection site. One hand was used to stretch the skin area to be swabbed (4 cm$^2$) and the other hand was used to rub the swab back and forth for 30 seconds, applying firm pressure to the skin. The swab was inserted into the tube from the ESwab sample collection kit according to manufacturer's protocol and stored at room temperature until processed (within 48 hours).

To obtain individual colonies of S. epidermidis, the ESwab was streaked onto TSB agar and incubated aerobically overnight at 37° C. Colonies resembling S. epidermidis were re-streaked onto Mannitol Salt agar for further identification. Colonies that were able to grow well on the Mannitol Salt agar without producing a color change from red to yellow were likely to be S. epidermidis isolates. Nine isolates that physically resembled S. epidermidis species were initially identified by growth on Mannitol Salt agar. The high salt concentration of the agar is specific for the growth of the genus Staphylococcus. Most pathogenic Staphylococci can ferment mannitol and will produce a color change from red to yellow when grown on Mannitol Salt agar. Potential S. epidermidis isolates were, therefore, identified by their abilities to grow on the Mannitol Salt agar, but not produce a color change as seen in FIG. 1. Four of the isolates that grew well on the Mannitol Salt Agar and did not produce a color change from red to yellow were further identified by 16S rRNA sequencing. BLAST results of all four isolates that were analyzed by 16S rRNA sequencing showed a greater than 99% sequence similarity to S. epidermidis species. One selected isolate was named MK022B.

Example 4: Preparation of S. epidermidis MK022B Complex

Glycerol, sucrose, β-lactose, and D-(+)-maltose were purchased from Sigma-Aldrich. Stock solutions of each prebiotic (4% w/v) were prepared in water and filtered through a 0.22 µm filter for sterilization.

S. epidermidis isolate MK022B obtained as described was cultured on trypic soy broth (TSB) agar plates at 37° C. An inoculum of S. epidermidis was prepared by suspending one colony of S. epidermidis into 7 ml of TSB broth and growing at 37° C., 215 RPM overnight. The overnight culture was subcultured 1:100 in fresh TSB. Once mid-log phase was reached, the cells were pelleted by centrifugation, washed and resuspended in fresh PBS. In 15 ml culture tubes, 4.9 ml of Rich Broth (20 g/L yeast extract, 6 g/L TSB) was combined with 40 µl 0.5% phenol red indicator, 5 ml of 4% prebiotic (glycerol, sucrose, β-lactose, or D-(+)-maltose) or PBS as a control, and S. epidermidis ($10^5$ CFU/ml) and placed in an anaerobic Gas-Pak (BD). The cultures were incubated at 37° C., 215 RPM for 5 days to determine if the S. epidermidis strains were able to ferment the sugars. If the culture changed from red to yellow, suggesting fermentation had occurred, new cultures were setup as described above without the addition of phenol red and incubated anaerobically for 14 days.

Following a 5 day anaerobic incubation in the presence of phenol red, the S. epidermidis cultures containing glycerol, sucrose, D-(+)-maltose and β-lactose showed a change of color from red to yellow for both the S. epidermidis ATCC 12228 strain and the S. epidermidis isolate MK022B indicating fermentation had occurred (FIG. 2). A color change was not seen for either S. epidermidis strains for the PBS control (FIG. 2). The acidification of the media was due to the formation of short chain fatty acids from the fermentation of the different sugars by S. epidermidis.

Following a separate 14 day fermentation, the cells were pelleted by centrifugation (4,000×g, 10 minutes, 4° C.) and the supernatants were filtered through a 0.22 µm filter for sterilization to obtain the conditioned media (designated MK022B Complex).

Similarly, S. epidermidis (ATCC 12228) and other S. epidermidis clinical isolates from 18-28 yrs old individuals with clear, radiant, healthy complexion were used to prepare S. epidermidis complexes.

Example 5: Testing of YM Complex and/or MK022B Complex in Human Keratinocytes The Complexes are incubated with human keratinocytes in vitro and changes in ceramide levels were recorded. The YM complex and MK022B complex preparations increases levels of ceramides.

Example 6: Formulation of YM Complex and MK0022B Complex for Testing in Human Subject for Skin Hydration and Appearance Including a Clear, Radiant, and Healthy Complexion The formulation include various formats including liquid, gel, lotion, and cream. Up to 75% of the aloe vera powder was dissolved in water. The YM and/or MK022B Complex (0.1-50%) was added to the mixture and stirred until dissolved. Algae extract with hyaluronate gel (10%) and glycerol (5%) was added to the mixture followed by 1% green tea extract. The solution was stirred until all components were dissolved. Sodium hydroxide was used to adjust the solution pH to 5.5 and the remaining aloe vera powder in water was used to bring the solution up to volume. Alternatively, for gel format, HE Cellulose (0.1-0.5%) was slowly added with vigorous stirring and the solution was stirred overnight until the desire consistency was obtained. Alternatively, individual microbial metabolites such as glutathione and/or lactic acid were added as a anti-oxidants and brightening agents. Alternatively, individual anti-ageing metabolites isolated from YM or MK022B microbiomes were added. Alternatively, vitamins such as vitamin C and/or E were added as anti-oxidants. Alternatively, other ingredients commonly used in skincare preparations were added.

Example 7: Testing of YM and MK022B Complexes in Human Keratinocytes

The YM and MK022B complexes are incubated with human keratinocytes in vitro and changes in ceramide levels are recorded. The YM and MK022B complex preparations that increase levels is selected for further studies.

Example 8: Formulation of YM and MK022B Complexes for Delivery into Skin

The formulation includes various formats including liquid, gel, lotion, and cream. The YM and MK022B complex preparations that increase levels of ceramides in keratinocytes are formulated for topical delivery. The formulation components are selected to allow for delivery of the complex into epidermis and stratum basale and contact with migrating keratinocytes. The formulations are tested for delivery into stratum corneum, epidermis and dermis using Franz Cell skin permeation assays in human skin.

Example 9: Testing of YM and MK022B Complexes in Human Subjects

Formulated YM and MK022B Complexes were tested in aged human volunteers (age 50+ years old). The formulation was applied to selected skin area two times per day. Placebo (PBS) was applied to control area. The subjects were asked to fill out questionnaire regarding appearance of their skin. The subjects indicated noticeable improvement in their skin appearance after 7 days (Table 1).

TABLE 1

Appearance of skin as assessed by human volunteers

| Sample tested | No change | Skin worsened | Skin improved |
|---|---|---|---|
| PBS | X | | |
| YM Complex | | | X |
| MK022B Complex | | | X |

The measurements are taken before and after 15-day treatment: The changes in the skin microbiome using sequencing, skin hydration using Corneometer, epidermal barrier function is evaluated by measuring the trans-epidermal water loss using the Tewameter. To assess the skin ceramide levels, stratum corneum sheets are removed by tape stripping. The samples are extracted for lipids and levels of ceramides are measured.

Example 10: Identification of Individual Metabolites with Anti-Ageing Properties Including Skin Barrier Function Improvement and Skin Healing Improvement Individual skin microbiome metabolites from the YM and MK0022B Complexes are identified by NMR and their derivatives such as prodrugs formed by preparing esters are prepared. The metabolites and their derivatives are formulated and tested in various assays as described in Examples 7-9.

Example 11: Preparation of Synthetic YM MK022B Complexes

Synthetic YM and MK022B Complexes are prepared that contain the optimal concentration of individual skin microbiome metabolites or their derivativess and prebiotic compounds. Alternatively, compounds that enable delivery of the Synthetic Complexes to the keratinocytes in the epidermis and stratum basale and are cosmetically acceptable are added.

Example 12: Development of Combination Product Candidates Containing YM and MK022B Complexes Combination product candidates are developed that contain YM and/or MK022B Complex and one or more other anti-aging compounds selected from the following compounds—Retinol (for instance, in the form of retinyl palmitate), Epidermal Growth Factor, alpha hydroxy acid, beta hydroxy acids, exfoliants, argireline, copper peptide, coenzyme Q10, anti-oxidants, niacinamide, hyaluronic acid, polylactic acid, *Boswellia serrata*, sunscreens or vitamin C, glutathione. The combination product is formulated and tested as described. and compared to the individual components alone. The combination product candidate that results in synergistic effect and yields the best quality and appearance of the skin is selected for the product.

Example 13: Transplanting the Skin Microbiomes

Skin microbiomes, such as YM prepared in Example 1 or MK022B prepared in Example 3, are transplanted to the skin of subjects with aging skin (on average 40+ yrs old). The transplantation is repeated daily for 2-14 days. The changes in the skin microbiome are analyzed by sequencing. The skin is also evaluated for the effect on skin properties as described in Example 9. Alternatively, the skin microbiomes are stabilized and preserved for storage by commonly used methods including freeze drying, spray drying and other methods that results in dried skin microbiome preparation. Alternatively, prebiotics (such as sugars that the bacteria in the microbiome use for fermentation) are added to the dried skin microbiome preparations for increased shelf life. The skin microbiome (+/− prebiotics) preparations are stored as a dry powder and reconstituted by adding water prior to the application to skin.

Example 14: Gut Probiotic Complexes with Anti-Ageing Properties

Anti-aging probiotics for the gut microbiome were formulated. For example, one probiotics strain formulation contained 1-30 Billion *Bacillus Subtilis* DE111, *Lactobacillus paracasei, Lactobacillus acidophilus, Bifidobacterium bifidum*. Alternatively, commonly used indigestible prebiotics were added. Alternatively, bacteriophages directed against undesirable gut bacteria, such as *E. coli* were added. Probiotics were prepared as tablets with acid resistant coating.

The probiotics were administered to subjects with aged skin and the changes in gut microbiome and skin appearance were evaluated. Subjects reported improvements in skin appearance (Table 2).

TABLE 2

Appearance of skin as assessed by human volunteers

| Sample tested | No change | Skin worsened | Skin improved |
|---|---|---|---|
| No gut probiotics | X | | |
| Gut probiotics | | | X |

Example 15: Anti-Aging Skincare Regiment

Human subjects used the following skincare regimen: Step One: Wash the skin in the morning and evening with a mild cleanser. Step Two: Apply the anti-aging preparation containing YM, MK022B, YM Complex, MK022B Complex, in the morning and in the evening. Apply any other skincare products, sunscreen, and makeup. Step Three: Take anti-aging probiotics once a day. Step Four: Repeat daily. Alternatively, zinc and other supplements and vitamins are added to the schedule. Alternatively, an application of a mask containing components of YM or MK022B is added to the regimen.

Other Embodiments

The detailed description set-forth above is provided to aid those skilled in the art in practicing the present invention.

However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method of treating skin of a human 50 years old or older, the method comprising contacting the skin with a skin microbiome complex,
wherein the skin microbiome complex comprises sterilized supernatant from a culture of microbiome bacteria that has been collected from a surface of wrinkle-free skin of a human subject 18-28 years old.

2. The method of claim 1, wherein the culture of microbiome bacteria was anaerobic.

3. The method of claim 1, wherein the skin microbiome complex further comprises an *S. epidermidis*.

4. The method of claim 2, wherein the culture comprises a carbohydrate that is fermented when cultured anaerobically.

5. The method of claim 4, wherein the carbohydrate is selected from the group consisting of at least one of glycerol, sucrose, β-lactose, D-(+)-maltose and galactose.

6. The method of claim 1, wherein the skin microbiome complex can increase ceramide levels when incubated with human keratinocytes.

7. The method of claim 1, wherein the skin microbiome complex is formulated in a liquid, gel, lotion, or cream.

8. The method of claim 1, wherein the skin microbiome complex further comprises one or more anti-aging compounds selected from the group consisting of retinol, epidermal growth factor, alpha hydroxy acid, a beta hydroxy acid, an exfoliant, argireline, a copper peptide, coenzyme Q10, an anti-oxidant, niacinamide, hyaluronic acid, polylactic acid, *Boswellia serrata*, a sunscreen, vitamin C and glutathione.

9. The method of claim 1, wherein the skin microbiome complex is contacted with the skin twice a day for at least 7 days, wherein the human notices improvement in their skin appearance after the 7 days.

10. The method of claim 1, wherein the skin microbiome complex is contacted with the skin twice a day for at least 15 days.

* * * * *